US00PP09053P

United States Patent [19]

Serimian et al.

[11] Patent Number: Plant 9,053

[45] Date of Patent: Feb. 7, 1995

[54] "AUGUST LION II" NECTARINE TREE

[76] Inventors: Donald M. Serimian; Lionel M. Serimian, both of 11024 E. Dinuba Ave., Selma, Calif. 93662

[21] Appl. No.: 260,041

[22] Filed: Jun. 15, 1994

[51] Int. Cl.[6] ..... A01H 5/00
[52] U.S. Cl. ..... Plt./41.1
[58] Field of Search ..... Plt. 41.1

*Primary Examiner*—James R. Feyrer
*Attorney, Agent, or Firm*—Worrel & Worrel

[57] ABSTRACT

A new and distinct variety of nectarine tree which is somewhat similar to the "Red Lion" nectarine tree (U.S. Plant Pat. No. 5,591) from which it was derived as a cross with the "Summer Lion" nectarine tree (U.S. Plant Pat. No. 6,544), but from which it is distinguished by producing fruit which are mature for harvesting and shipment approximately eight (8) days prior to the fruit produced by the "Red Lion" nectarine tree and wherein the fruit is of an outstanding quality having a very good flavor, a highly red blush skin coloration and superior eating quality.

1 Drawing Sheet

BACKGROUND OF THE NEW VARIETY

The present invention relates to a new and distinct variety of nectarine tree, which will hereinafter be denominated varietally as the "August Lion II" nectarine tree, and, more particularly, to a nectarine tree which produces large clingstone fruit which are mature for commercial harvesting and shipment approximately August 1 to August 8 in the San Joaquin Valley of central California and which have a firm flesh and an intense red blush skin coloration.

The successful development of new commercial varieties of fruit trees is, of course, dependent upon the market appeal of the fruit produced thereby. While the myriad of attributes which any given variety of fruit may possess is largely responsible for the commercial success or failure of the variety, there are other factors which may have a significant bearing thereon.

For example, there may be a substantial commercial advantage in being able to associate the new variety of fruit in the marketplace with an existing, highly successful commercial variety. This may be possible in a number of respects, but is perhaps most effective if the ripening period of the new variety is closely adjacent to that of the existing variety. Where the two varieties share closely similar attributes in other respects, the promise for success of the new variety is very bright indeed. The new variety of the present invention appears to be such a variety, as will hereinafter become more clearly apparent.

ORIGIN AND ASEXUAL REPRODUCTION OF THE NEW VARIETY

The present variety of nectarine tree hereof was discovered in 1982 by the inventors in their orchard located near Selma in the central San Joaquin Valley of California. The new variety is a cross between the "Red Lion" nectarine tree (U.S. Plant Pat. No. 5,591) and the "Summer Lion" nectarine tree (U.S. Plant Pat. No. 6,544). The inventors asexually reproduced the new variety in 1985 in the same orchard and observed the progeny over the next several growing seasons. The asexually reproduced trees first bore fruit in 1987. The inventors continued to observe the asexually reproduced trees throughout these years and until the present time and have confirmed that the progeny are identical to the parent in every respect.

SUMMARY OF THE NEW VARIETY

The nectarine tree is characterized by producing large clingstone fruit which have an intense red blush skin coloration and are ripe for commercial harvesting and shipment approximately August 1 to August 8 in the San Joaquin Valley of central California. The new variety is perhaps most closely similar to the "Red Lion" nectarine tree, but is distinguished therefrom by the aforementioned ripening date as well as in other respects. The new variety is uniquely well suited to extending, in effect, the length of the market for the "Red Lion" nectarine tree by ripening approximately eight days prior thereto.

BRIEF DESCRIPTION OF THE DRAWING

The accompanying drawing is a color photograph of portions of the nectarine tree of the present invention illustrating its distinctive characteristics including a first nectarine of the new variety disposed in plan view showing the apex end thereof; a second nectarine disposed in side elevation showing the suture thereof; a third nectarine sectioned along its longitudinal axis through the pit well and with the stone left in place; a stone disposed in plan view; and representative foliage of the new variety.

DETAILED DESCRIPTION

Referring more specifically to the pomological details of this new and distinct variety of nectarine tree, the following has been observed under the ecological conditions prevailing at the orchard of origin which is located near Selma in the San Joaquin Valley of central California. All major color code designations are by reference to the *Dictionary of Color,* by Maerz and Paul, Second Edition, 1950. Common color names are also occasionally employed.

TREE

Generally: Hardy as grown under climatic conditions typical in central San Joaquin Valley.

*Figure.*—Upright-spreading with eventual form and tree density determined by pruning.

*Productivity.*—Very productive.

*Regularity of bearing.*—Regular.

Trunk:

*Size.*—Average diameter.

*Surface texture.*—Average.

*Color.*—Greyish-brown (7-C-10).

*Lenticels — numbers.*—Numerous.

*Lenticels — size.*—Large lenticels present, surrounded by dark hazel-brown (13-J-10) callous tissue.

Branches:

*Size.*—Average.

*Surface texture.*—Average.

*Color — one year or older wood.*—Medium brown (15-E-11).

*Color — immature branches.*—Light green (18-G-5) with surfaces exposed to direct sunlight tinged with red.

*Surface texture — current season's shoots.*—Smooth.

LEAVES

Size:

*Generally.*—Large. Leaf measurements are taken from leaves growing at midpoint of vigorous current season's shoots.

*Average length.*—19.3 mm (0.7598 inches), including petiole.

*Average width.*—4.6 mm (0.1811 inches).

Form: Lanceolate with acuminate leaf tip. Tip often twisted to one side.

Color:

*Upwardly disposed surface.*—Medium green (23-J-3).

*Downwardly disposed surface.*—Grey-green (22-G-5).

*Leaf vein.*—Mid-vein on lower leaf surface a yellow-green (19-J-5).

Marginal form:

*Generally.*—Crenate with broad, low and usually regular crenations.

Leaf margin: Slightly undulate.

Glandular characteristics: Glands medium to large in size and most frequently reniform in shape, although occasionally globose forms can be found. A range of numbers from 2 to 4 are most commonly present. Gland location is variable with the most common pattern being from 2 to 3 glands present on the petiole in alternate position and one or more glands present on the base of the leaf margin. Gland color is a shiny yellow-green (18-K-6) which darkens with advancing maturity.

Petiole:

*Size.*—Moderately long.

*Length.*—Averages from 11 mm (0.4331 inches) to 14 mm (0.5512 inches).

*Thickness.*—Averages from 1.5 mm (0.0591 inches) to 2.0 mm (0.0787 inches).

*Color.*—Yellow-green (18-J-4).

Stipules: Two small stipules present subtending the petiole, 5 mm (0.1969 inches) to 6 mm (0.2362 inches) in length and with serrated margins. Stipules are early deciduous.

*Color.*—Greenish-yellow (17-K-7), darkening with age.

FLOWERS

Flower buds:

*Size.*—Medium.

*Form.*—Conic and covered with a heavy grey pubescence.

Flower bud scales:

*Color.*—Chestnut brown (8-J-9).

Flowers:

*Generally.*—Bloom was observed in producing trees of the new variety in March of 1990, near Selma in the San Joaquin Valley of central California. Number of chilling hours accumulated in the general Fresno County fruit growing district during the 1989-1990 winter season as well over thirteen hundred (1300) hours. This is the number of hours at or below forty-five degrees (45°) Fahrenheit and represents a colder than average winter chilling season.

*Date of full bloom.*—Mar. 19, 1990. Mid season in relation to the bloom of other common commercial nectarine varieties.

*Bloom quantity.*—Abundant bloom present. Buds average 1 to 2 per node, most commonly 2 per node.

Size:

*Generally.*—Large, showy type flower.

*Diameter.*—Fully expanded bloom 31 mm (1.220 inches) to 35 mm (1.378 inches).

Petals:

*Size.*—Large.

*Length.*—19 mm (0.7480 inches) to 22 mm (0.8661 inches).

*Width.*—14 mm (0.5512 inches) to 16 mm (0.6299 inches).

*Form.*—Broadly ovate.

*Color.*—Light pink (1-D-2) when young, darkening with age especially in the basal area of the petal claw.

Petal claw:

*Form.*—Truncate and moderately broad.

Petal margin: Undulate, especially apically.

Petal apex: Rounded.

Pedicel:

*Length.*—Medium. 2.5 mm (0.0984 inches) to 3.0 mm (0.1181 inches).

*Thickness.*—Averaging 1.5 mm (0.0591 inches).

*Color.*—Shiny green (19-J-3).

Nectaries:

*Color.*—Orange (12-J-11) when young, darkening somewhat and becoming dull in color with age.

Anthers:

*Size.*—Medium.

Pollen: Abundant.

Color.—Yellow (9-K-2).

Stamens:

*Length.*—Averaging 15 mm (0.5906 inches) to 18 mm (0.7087 inches). The stamens are equal to or slightly shorter than the flower pistil.

Filament:

*Color.*—Light pink (1-C-7) when young, darkening with age to a violet (2-G-3).

Pistil:

*Length.*—Averaging 18 mm (0.7087 inches) to 20 mm (0.7874 inches), including the ovary.

*Color.*—Light green-yellow (17-H-3).

*Surface.*—The pistil and ovary surfaces are glabrous.

FRUIT

Maturity when described: Ripe for commercial harvesting and shipment approximately August 1 to August 8 in 1989, or about eight days before the fruit of the "Red Lion" nectarine tree, near Selma in the San Joaquin Valley of central California. Ripening date can vary depending upon variations in climatic conditions such as in 1993 when the corresponding ripening dates were August 5 to August 15 and yet still about eight days before the fruit of the "Red Lion" nectarine tree.

Size:

*Generally.*—Uniform, large.

*Average diameter in the cheek plane.*—73 mm (2.874 inches).

*Average diameter in the axial plane.*—78 mm (3.071 inches).

*Average diameter in the suture plane.*—74 mm (2.913 inches).

Form:

*Uniformity.*—Uniform. Generally globose to ovate in lateral aspect. Generally globose in apical aspect.

*Symmetry.*—Usually asymmetrical.

Suture:

*Generally.*—A shallow groove from apex to base, more deep near the fruit apex. The suture takes on the coloration of the underlying ground or blush color. Some red (8-J-6) striping occurs along the suture, usually more evident at mid-suture and basally.

Ventral surface:

*Generally.*—Rounded and slightly lipped. Lipping is usually stronger on one half and over the apical shoulder. One half of the fruit is usually larger than the other.

Stem cavity:

*Generally.*—Medium.

*Width.*—22 mm (0.8661 inches) to 23 mm (0.9055 inches).

*Depth.*—Medium.

*Length.*—25 mm (0.9843 inches) to 26 mm (1.024 inches).

*Shape.*—Usually oval. A tight ventral suture crease usually present within the cavity.

Stem:

*Size.*—Medium.

*Length.*—15 mm (0.5906 inches) to 18 mm (0.7087 inches).

*Thickness.*—4 mm (0.1575 inches) to 5 mm (0.1969 inches).

*Color.*—Green-yellow (17-K-5).

Apex:

*Shape.*—Generally rounded.

Pistil point: Only very slightly raised. Pistil point usually oblique. Most frequently a depression is present on both the ventral and dorsal sides of the apex.

Base: Rounded. Base angle is usually slightly oblique to the fruit axis.

Skin:

*Thickness.*—Average with mild flavor.

*Texture.*—Tenacious to flesh at commercial maturity. Glabrous. Bright, shiny finish.

*Tendency to crack.*—No observed tendency to crack.

*Blush color.*—Highly colored for season of maturity, 70 percent to 100 percent blushed. Blush color is an intense cherry red (6-K-11) with darker shade tones to a deep garnet-red(7-J-6). This general blush color is present with the darker tones occurring basally and overlain with dark red (8-J-6) mottling and striping. Striping most apparent basally and along the ventral suture. Mottling most apparent laterally and apically.

*Ground color.*—Yellow-amber (10-K-4).

Flesh:

*Color.*—Yellow-amber (9-K-3), slightly lighter next to the skin.

*Surface of pit cavity.*—Red (6-L-10) with red coloration radiating outward into the flesh from the center.

*Juice production.*—Juicy.

*Flavor.*—Very good. High flavored with good balance.

*Aroma.*—Moderate.

*Texture.*—Firm at commercial maturity, softening and becoming juicy with advancing maturity.

*Fibers — numbers.*—Few, short, light colored flesh fibers present.

*Fibers — texture.*—Tender.

*Ripening.*—Even.

*Eating quality.*—Superior.

Stone:

*Attachment.*—Full clingstone, held tightly in pit cavity.

*Fibers — numbers.*—Moderate.

*Fibers — length.*—Relatively short.

*Size — generally.*—*Large.*

*Size — length.*—Averages 41 mm (1.614 inches) to 44 mm (1.732 inches).

*Size — width.*—27 mm (1.063 inches) to 30 mm (1.181 inches).

*Size — thickness.*—20 mm (0.7874 inches) to 22 mm (0.8661 inches).

*Form — generally.*—Obovate to nearly oval.

*Apex — shape.*—Acute.

*Color — dry.*—Tan-brown (13-H-8) with considerable purple staining.

*Base — shape.*—Moderately truncate in form. Base angle slightly oblique to nearly at right angle to the stone axis.

*Sides — generally.*—Nearly equal. Side surfaces very coarse with deep ridges over the apical shoulders and deep pits and grooves over the lateral surfaces and basally.

*Hilum.*—Large with a well defined and grooved collar surrounding the hilum.

*Ventral edge.*—Very broad with several low wings converging apically.

*Dorsal edge.*—Coarse with a groove from base to apex. Groove moderately wide 2.0 mm (0.0787 inches) at base, becoming more narrow at mid-edge and tight at apex.

*Apical shoulder.*—Somewhat eroded and concave.

*Ridges.*—Dorsal edge ridges are high and prominent, especially at mid-stone.

*Tendency to split.*—None observed.

Use: Fresh market nectarine for use in local market and long distance shipping.

Keeping quality: Good.

Although the new variety of nectarine tree possesses the described characteristics noted above as a result of the growing conditions prevailing near Selma in the San Joaquin Valley of central California, it is to be understood that variations of the usual magnitude and characteristics incident to changes in growing conditions, irrigation, fertilization, pruning, pest control, climatic variation and the like are to be expected.

Having thus described and illustrated our new variety of nectarine tree, what we claim as new and desire to be secured by Plant Letters Patent is:

1. A new and distinct variety of nectarine tree substantially as illustrated and described which is somewhat similar to the "Red Lion" nectarine tree (U.S. Plant No. 5,591) from which it was derived as a cross with the "Summer Lion" nectarine tree (U.S. Plant Pat. No. 6,544), but from which it is distinguished by producing fruit which are mature for commercial harvesting and shipment approximately August 1 to August 8, or about eight days before, the "Red Lion" nectarine tree, in the San Joaquin Valley of central California and which has an intense red blush skin coloration.

* * * * *

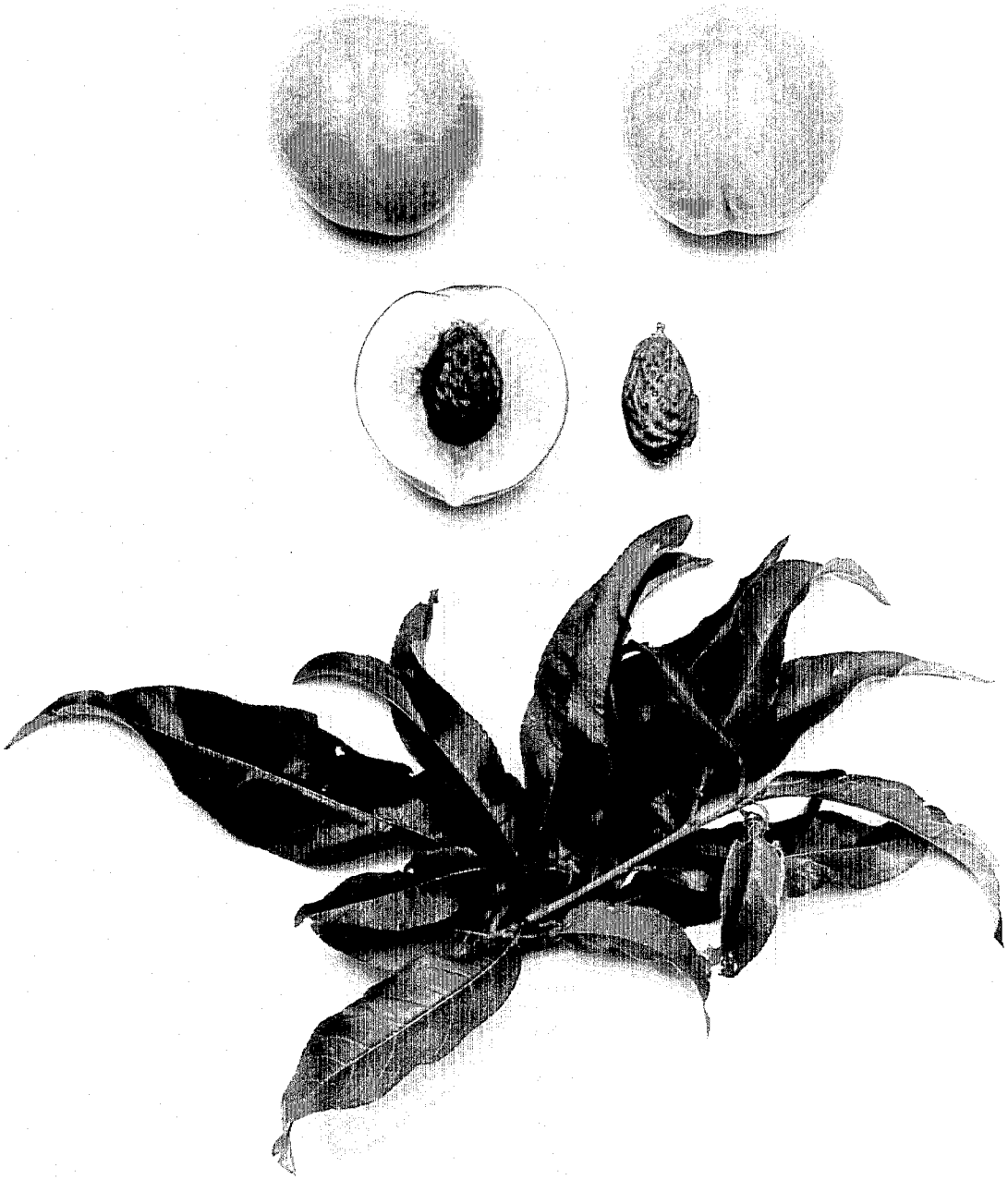

UNITED STATES PATENT AND TRADEMARK OFFICE

CERTIFICATE OF CORRECTION

PATENT NO. : PP 9,053

DATED : FEBRUARY 7, 1995

INVENTOR(S) : DONALD M. SERIMIAN; LIONEL M. SERIMIAN

It is certified that error appears in the above-identified patent and that said Letters Patent is hereby corrected as shown below:

Column 4, Line 11, delete "as" and substitute

---was---.

Signed and Sealed this

Twelfth Day of September, 1995

*Attest:*

*Attesting Officer*

Bruce Lehman

BRUCE LEHMAN

*Commissioner of Patents and Trademarks*